United States Patent [19]

Bergman

[11] Patent Number: 4,723,913
[45] Date of Patent: Feb. 9, 1988

[54] DENTAL IMPLANT

[76] Inventor: Harold Bergman, 1905 - 808 Nelson Street, Vancouver, British Columbia, Canada, V6Z 2H2

[21] Appl. No.: 881,917

[22] Filed: Jul. 2, 1986

[51] Int. Cl.$^4$ ............................................... H61C 8/00
[52] U.S. Cl. ..................................................... 433/173
[58] Field of Search ................ 433/173, 174, 175, 176

[56] References Cited

U.S. PATENT DOCUMENTS

| | | | |
|---|---|---|---|
| 3,499,222 | 3/1970 | Linkow et al. | 433/174 |
| 4,062,119 | 12/1977 | Linkow et al. | 433/176 |
| 4,379,694 | 4/1983 | Riess | 433/173 |

Primary Examiner—Robert Peshock
Attorney, Agent, or Firm—Christie, Parker & Hale

[57] ABSTRACT

A dental implant. The dental implant has a body having a top and bottom and parallel sides extending from the top to the bottom. There is at least one opening extending generally diametrically through a lower part of the body. A plurality of discrete, circumferential grooves are formed at the top of the body. The grooves are about 10 to 120 microns wide and about 10 to 100 microns deep. There is an opening in the top to receive a dental receptor. The grooves in the implant prevent cell growth along the length of the implant. Such growth weakens the location of prior art implants.

15 Claims, 8 Drawing Figures

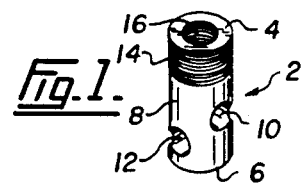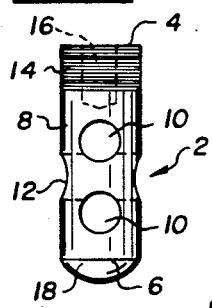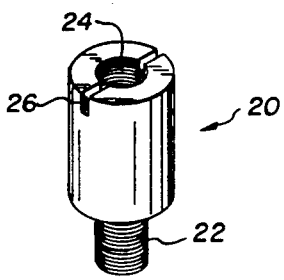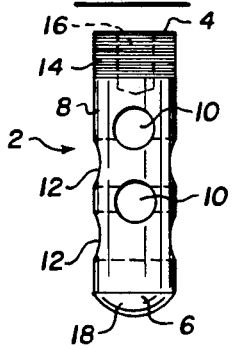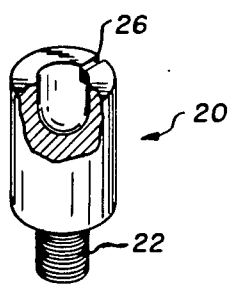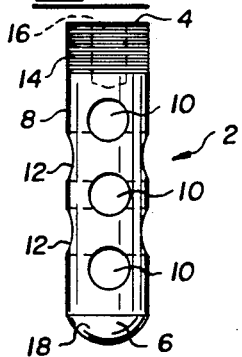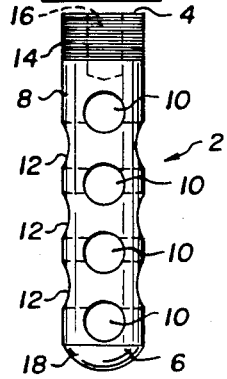

DENTAL IMPLANT

FIELD OF THE INVENTION

This invention relates to a dental implant.

DESCRIPTION OF THE PRIOR ART

A dental implant is a means of attaching a dental fitting, for example a bridge or the like, in the mouth of a patient. The implant is located in the jaw of the patient and, subsequently, the dental fitting is located in it.

A problem with prior art dental implants is that fibroblast and epithelial cell migration takes place down the implant, on its outer surface, thus loosening the implant in the jaw of the patient.

The present invention overcomes this disadvantage and provides a dental implant in which, in experimental observation so far, deleterious cell growth, as outlined above, has not been seen.

SUMMARY OF THE INVENTION

Accordingly the present invention is a dental implant comprising a body having a top and bottom and parallel sides extending from the top to the bottom; at least one opening extending generally diametrically through a lower part of the body; a plurality of discrete, circumferential grooves at the top of the body, the grooves being about 10 to 120 microns wide and about 10 to 100 microns deep; and an opening in the top to receive a dental receptor.

The presence of discrete, circumferential grooves of the defined dimensions at the top of the body have been found effective in preventing the tissue ingrowth that is the disadvantage in prior art implants.

DRAWINGS

Aspects of the invention are illustrated, merely by way of example, in the accompanying drawings in which:

FIG. 1 is a perspective view of a dental implant according to the present invention;

FIGS. 2 through 5 are side elevations of varying sizes of embodiments of the present invention;

FIG. 6 illustrates a device useful with the implant of FIG. 1;

FIGS. 7 and 8 show fittings useful with the present invention.

DESCRIPTION OF THE PREFERRED EMBODIMENTS

In the drawings FIG. 1 shows a dental implant comprising a body 2 having a top 4 and a bottom 6 and parallel sides 8 extending from the top to the bottom. There are openings 10 and 12 extending generally diametrically through the lower part of the body 2. In the FIG. 1 embodiment, the openings 10 and 12 overlap in part with each other, on the length of the implant. The same arrangement is shown in FIGS. 2 to 5. Indeed the embodiments of FIGS. 2 through 5 differ only in their length.

At the top of the body 2 there are a plurality of discrete, circumferential grooves 14. These grooves 14 are about 10 to 120 microns wide and about 10 to 100 microns deep.

There is an opening 16 in the top of the body 2 to receive a conventional dental fitting or receptor.

Preferably these implants are made of titanium or a titanium aluminum vanadium alloy of composition Ti $Al_6$ $Va_4$. Titanium and this alloy have a high capacity for osseointegration; that is they permits bone attachment over its surface. The alloy has the virtue of being easier to machine.

The drawings illustrate that the base of the implant is preferably rounded at 18, to facilitate fitting a hole formed in the jaw. Typically the hole in the jaw is drilled and has a rounded base so that the rounding of the implant at 18 helps to provide a close fit in the drill hole.

The openings 10 and 12 extending through the body, typically are about 2.0 mm in diameter, to facilitate location of the implant by increasing surface area. Where more than one opening is formed it is desirable that neighbouring openings be on diameters of the body at 90° to each other. It is also preferable that neighbouring openings overlap each other, again to facilitate growth of bone through the implant in the gum. These openings may be at 1.5 mms. centres along the body, assuming that the body is long enough to permit a plurality of openings to be used, that is the distance between a centre line of one opening and the centre line of its perpendicular neighbour is preferably about 1.5 mms.

The opening 16 in the top 4 is desirably threaded. It receives a receptor 20 as shown in FIG. 7 provided with a correspondingly threaded portion 22. The receptor 20 may be provided with a ball and socket attachment as shown in FIG. 8 for a dental fitting or may be internally threaded at 24 to receive the fitting. Apart from the provision of the threaded portion 22 the fittings are conventional. Slot 26 is used to attach fitting 20. That is, slot 26 allows a blade to be used to rotate the device.

FIG. 6 shows a plug 28 to seal off the opening 16 in the top 4. Preferably the plug 28 is brightly coloured, the preferred colour being blue. This is because the implant is inserted in the gum and then left until it becomes properly implanted in the gum. At that time the receptor is attached to it. It is therefore desirable to seal off the top of the unused implant with a plug. If gum tissue grows over it, it is preferable that the plug be brightly coloured so it can be seen. The plug 28 is, of course, removed before the receptor is attached.

Typically the implants of the present invention will be 4 mm in diameter. They are made in lengths of 8, 10, 13 and 15 mms. The length of the area occupied by grooves 14 is typically about 1 mm. Opening 16 will be about 2.5 mm is diameter.

With the dental implants of the invention epithelial and fibroblast cell growth takes place along the grooves but not between them. Thus all migration that tends to loosen the implant is prevented.

I claim:

1. A dental implant comprising:
   a body having a top and bottom and parallel sides extending from the top to the bottom;
   at least one opening extending generally diametrically through a lower part of the body;
   a plurality of discrete, circumferential grooves at the top of the body, the grooves being about 10 to 120 microns wide and about 10 to 100 microns deep; and
   an opening in the top to receive a dental receptor.

2. A dental implant as claimed in claim 1 and made of titanium or an alloy of titanium of composition Ti $Al_6$ $Va_4$.

3. A dental implant as claimed in claim 1 in which the implant has a rounded base.

4. A dental implant as claimed in claim 1 including one or more of said openings extending through the body wherein each opening is about 2.0 mm in diameter.

5. A dental implant as claimed in claim 4 including a plurality of said openings along the length of the body.

6. A dental implant as claimed in claim 5 in which the neighbouring openings are on diameters of the body, at about 90° to each other.

7. An implant as claimed in claim 6 in which neighbouring openings are on about 1.5 mms. centres.

8. A dental implant as claimed in claim 6 in which each opening overlaps with its neighbouring opening or openings.

9. A dental implant as claimed in claim 1 in which the opening in the top is threaded.

10. A dental implant as claimed in claim 1 including a plug to seal off the opening in the top.

11. A dental implant as claimed in claim 1 in which the plug is brightly coloured.

12. A dental implant as claimed in claim 11 in which the colour is blue.

13. A dental implant comprising:
    a body having a top, a bottom, and an outer surface extending from the top to the bottom of the body;
    at least one opening extending generally diametrically through a lower portion of the body;
    a plurality of discrete circumferential grooves formed in the top portion of the outer surface of the body immediately below the top of the body, in which the grooves have a width of about 10 to about 120 microns and a depth of about 10 to about 100 microns so that the grooves inhibit the type of tissue ingrowth along the length of the implant that tends to loosen the implant when the implant is placed in the jaw of a patient; and
    an opening in the top of the body to receive a dental receptor.

14. A method for inhibiting tissue ingrowth along the length of a dental implant of the type having a body with a top, a bottom, and an outer surface extending from the top to the bottom of the body, and an opening in the top of the body to receive a dental receptor, the method comprising:
    providing a plurality of discrete circumferential grooves in the top portion of the outer surface of the body immediately below the top of the body, in which the grooves have a width of about 10 to about 120 microns and a depth of about 10 to about 100 microns; and
    placing the implant in the jaw of a patient so the circumferential grooves are effective to inhibit the type of tissue ingrowth along the length of the implant that tends to otherwise loosen the implant.

15. The method according to claim 14, including providing at least one opening extending generally diametrically through a lower part of the body for increasing the surface area and, therefore, the area in contact with the tissue of the jaw.

* * * * *